United States Patent [19]

Hu et al.

[11] Patent Number: 5,252,345
[45] Date of Patent: Oct. 12, 1993

[54] ZEOLITE COMPOSITIONS
[75] Inventors: Patrick C. Hu, Baton Rouge; James S. Staton, Pride; Karl E. Wiegand, Baton Rouge, all of La.
[73] Assignee: Ethyl Corporation, Richmond, Va.
[21] Appl. No.: 649,417
[22] Filed: Feb. 1, 1991

Related U.S. Application Data

[63] Continuation of Ser. No. 153,456, Feb. 8, 1988, abandoned.
[51] Int. Cl.$^5$ .............................................. A61K 33/06
[52] U.S. Cl. ................................................... 424/684
[58] Field of Search ......................................... 424/684
[56] References Cited

U.S. PATENT DOCUMENTS

| | | | |
|---|---|---|---|
| 3,836,676 | 9/1974 | Komakine | 426/74 |
| 4,515,780 | 5/1985 | Laurent et al. | 424/154 |
| 4,529,593 | 7/1985 | Warrell, Jr. et al. | 424/127 |
| 4,537,771 | 8/1985 | Greb et al. | 424/154 |
| 4,556,564 | 12/1985 | Laurent et al. | 426/2 |
| 4,610,883 | 9/1986 | Laurent et al. | 424/684 |
| 4,847,085 | 7/1989 | Laurent et al. | 424/684 |

FOREIGN PATENT DOCUMENTS

| | | |
|---|---|---|
| 939186 | 1/1974 | Canada. |
| 0119992 | 9/1984 | European Pat. Off. . |
| 0201804 | 4/1985 | European Pat. Off. . |
| 59-203450 | 11/1984 | Japan . |

OTHER PUBLICATIONS

Chung et al, *Nongsa Sihom Youngu Pogo*, 1978, 20 (livestock), pp. 77–83.
Mumpton et al, The Application of Natural Zeolites in Animal Science and Aquaculture, *Journal of Animal Science* 45, No. 5, 1188–1203 (1977).
Willis et al, *Poultry Science* 61, 438–442 (1982).
Vest et al, *Zeo-Agriculture '82.*
Nakaue, *Poultry Science*, 60, 944–949 (1981).
*Great Lakes Science Advisory Board of the Internat'l Joint Commission on the Health Implications of Non-NTA Deterg. Bldrs.*, Oct. 1980, Rev. Mar. 1981.
Gloxhuber et al, *Chemical Toxicology* 21:2, pp. 209–220 (1983).
Nolen et al, *Food & Cosmetic Toxicology*, 21 (5), p. 697 (1983).
Cook et al, Zeolite A Hydrolysis & Degradation, *Environ Sci. Technol.* 16(6), pp. 344–350 (1982).
Benke et al, *Food & Cosmetic Toxicology*, 17, pp. 123–127 (1979).
Anon, *Tentative Evaluation of the Health Aspects of Certain Silicates as Food Ingredients* (1977).
Carlisle, *Nutrition Reviews* 40(7), pp. 193–198 (1982).
Carlisle, Chap. 4, *Silicon & Siliceous Structures in Biol. Systems* Simpson, T. L., ed. B. E. Springer Verlag, NY (1981) pp. 69–94.
Berlyne et al, *Nephron*, 43, pp. 5–9, (1986).
Charnot et al, *Annales D' Endocronologie*, 32, pp. 397–402 (1971).
Charnot et al, Silicon Endocrine Bal. & Min. Metabolism, in Biochem of Silicon & Related Prod.'s, Bendz et al, Ed. Plenum Press, NY pp. 269–280 (1979).
Merkley et al, *Poultry Science* 62, pp. 798–804 (1983).
Reagan, Luther M., Effects of Adding Zeolites to the Diets of Broiler Cockerels; Thesis; Colo. State Univ., Apr. 25, 1984.
Edwards, *Poultry Science*, vol. 65, Supp. No. 1 (1986).
Roland et al, *Poultry Science* 64, 1177–87 (1985).
Miles et al, *Nutrition Reports International* 34, No. 6, 1097 (Dec., 1986).
Ingram et al, *Influence of ETHACAL® Feed Component on Production Parameters of White Leghorn Hens During High Temp.'s*—1986.

Primary Examiner—Frederick E. Waddell
Assistant Examiner—T. J. Criares
Attorney, Agent, or Firm—Richard J. Hammond

[57] ABSTRACT

A composition containing a zeolite and an acid suitable for use in increasing bone strength in an animal having a bone strength less than desired and/or for use in treating, preventing or delaying the onset of a bone disorder such as osteoporosis, osteochondrosis, or dyschondroplasia. A preferred zeolite is zeolite A. Preferred acids are illustrated by citric, fumaric and aspartic acids. The presence of such acids in the composition enhances the breakdown (i.e. decomposition) of the zeolite thereby making it more efficacious for increasing bone strength or combating bone disease. Preferably, the compositions contain from about 35 to about 65 weight percent of the acid; the remainder being the zeolite. Such compositions can be admixed with other materials such as excipients used in the preparation of unit dosage forms.

20 Claims, 5 Drawing Sheets

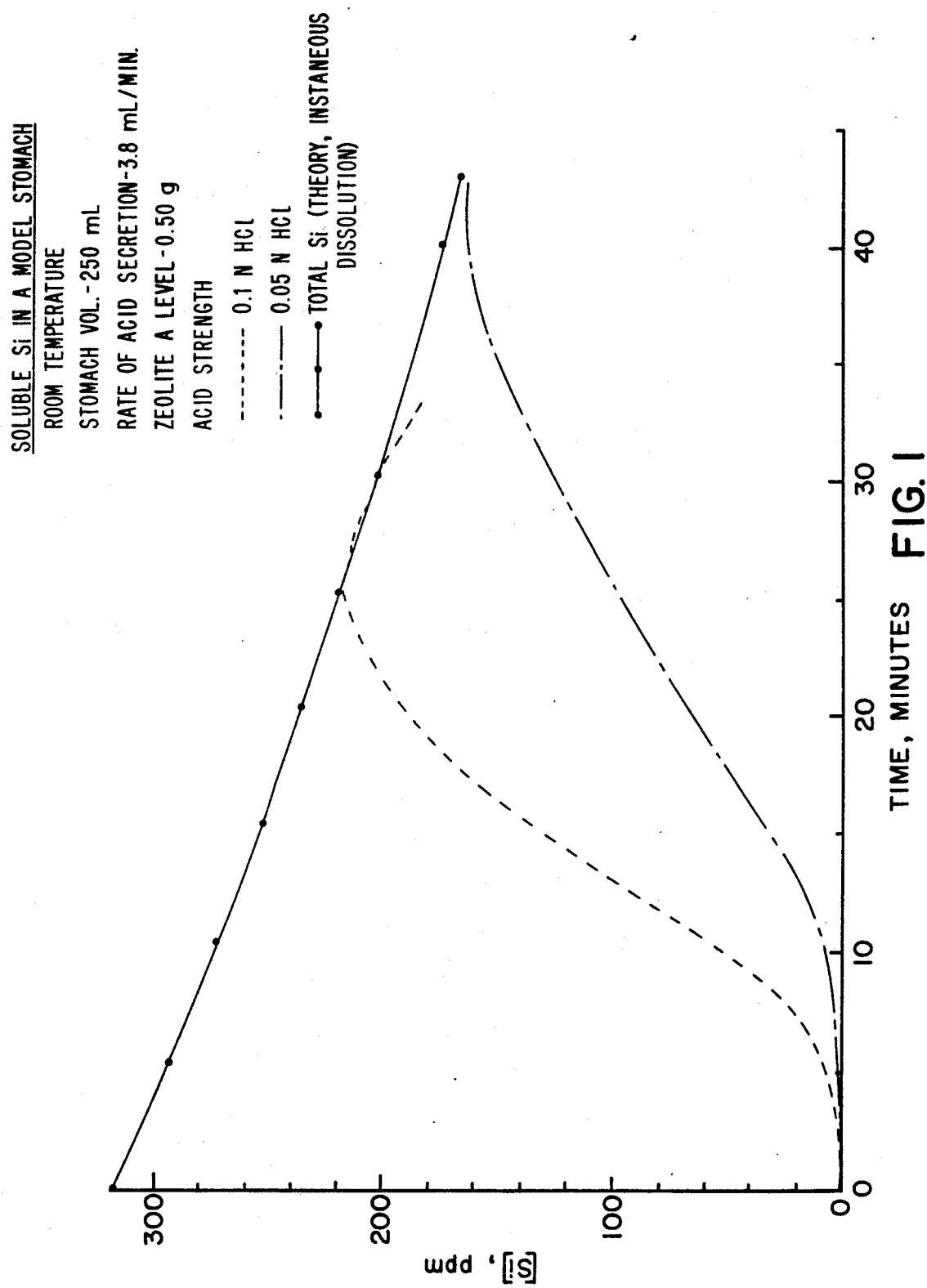

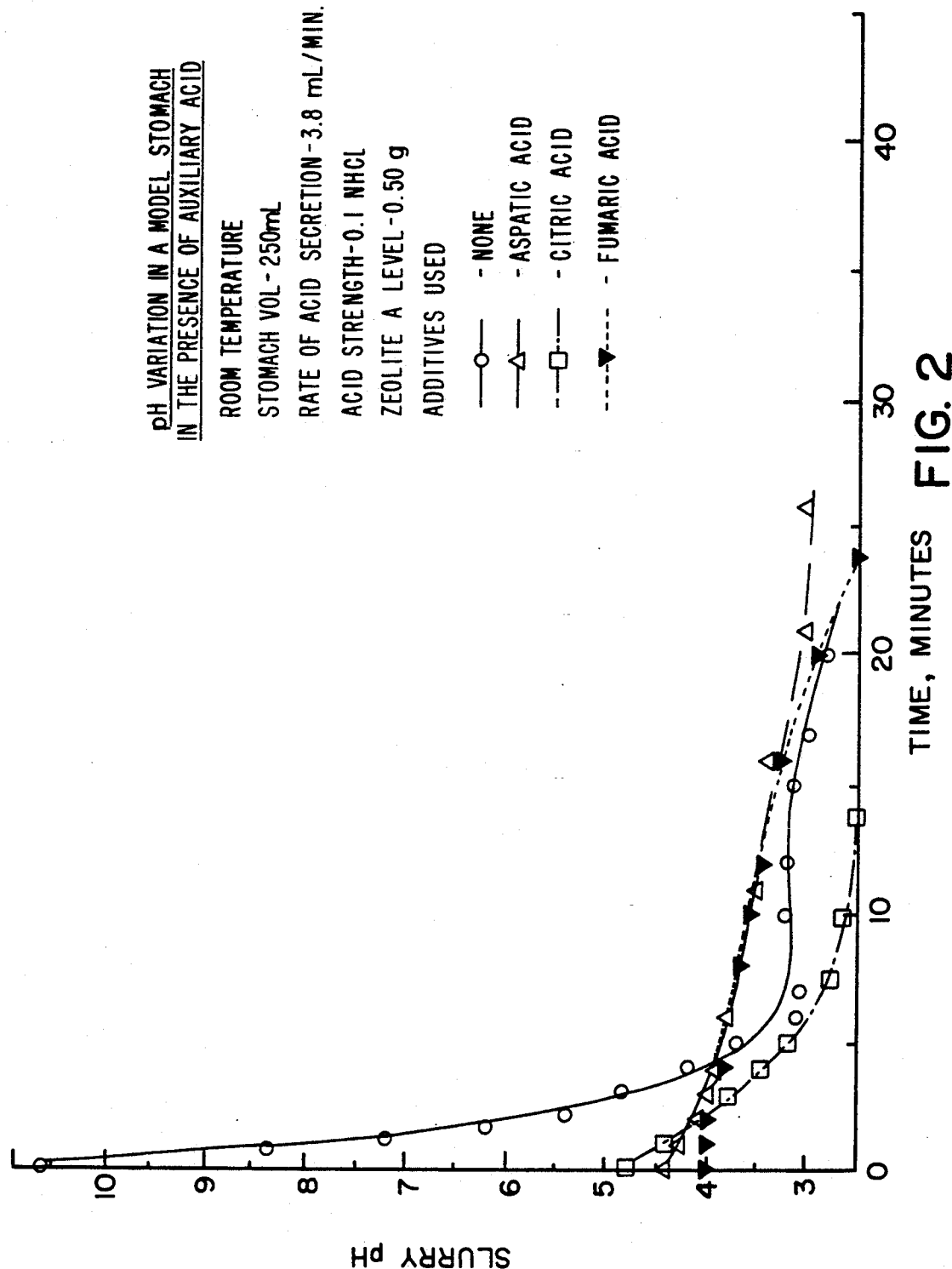

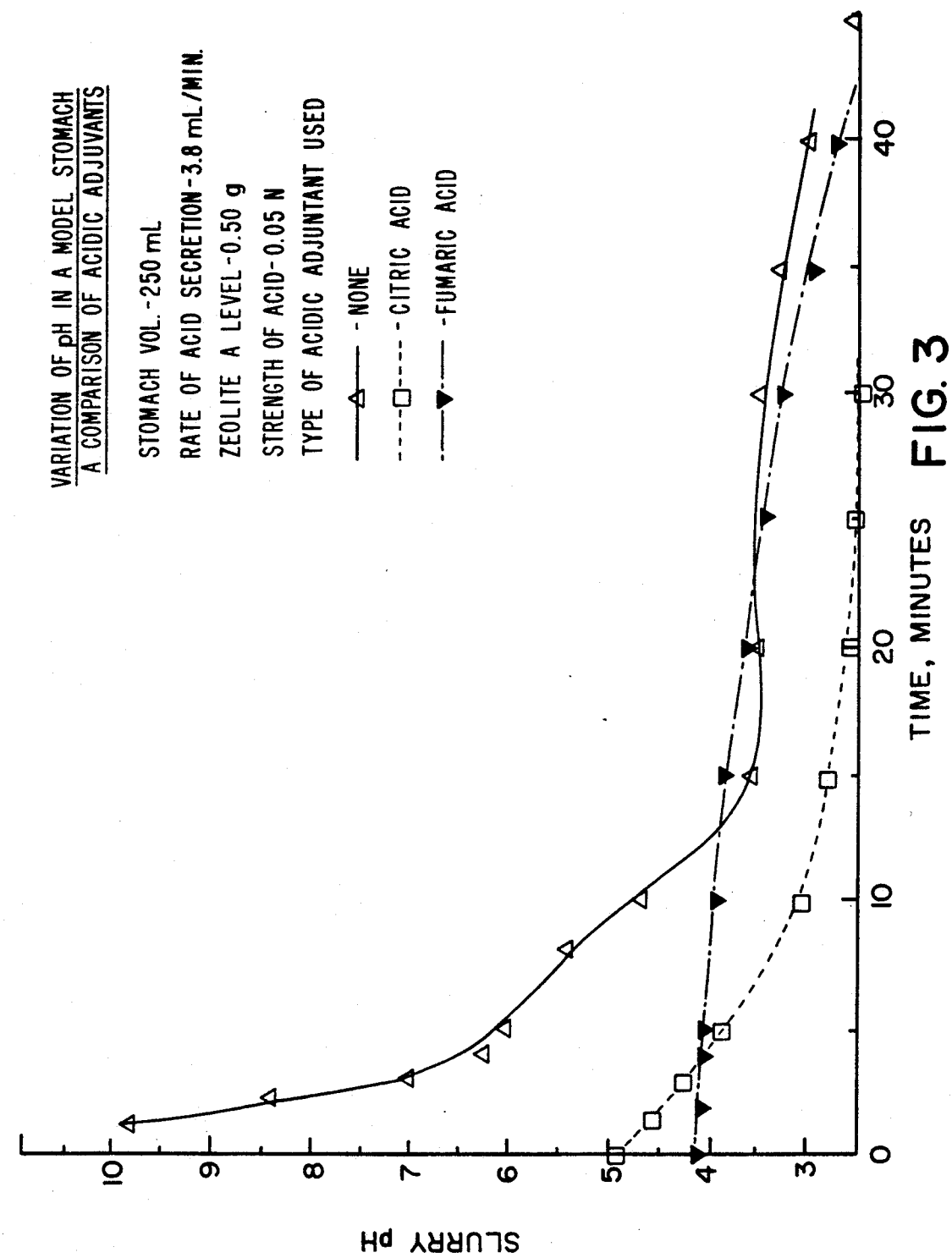

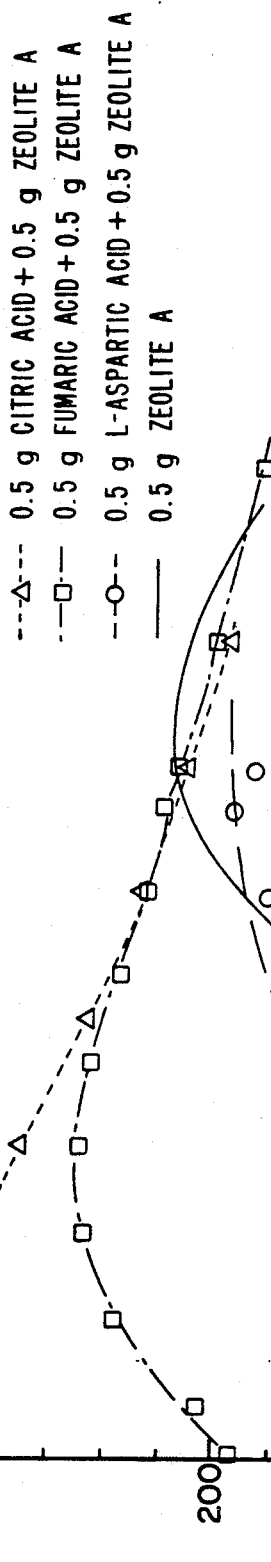

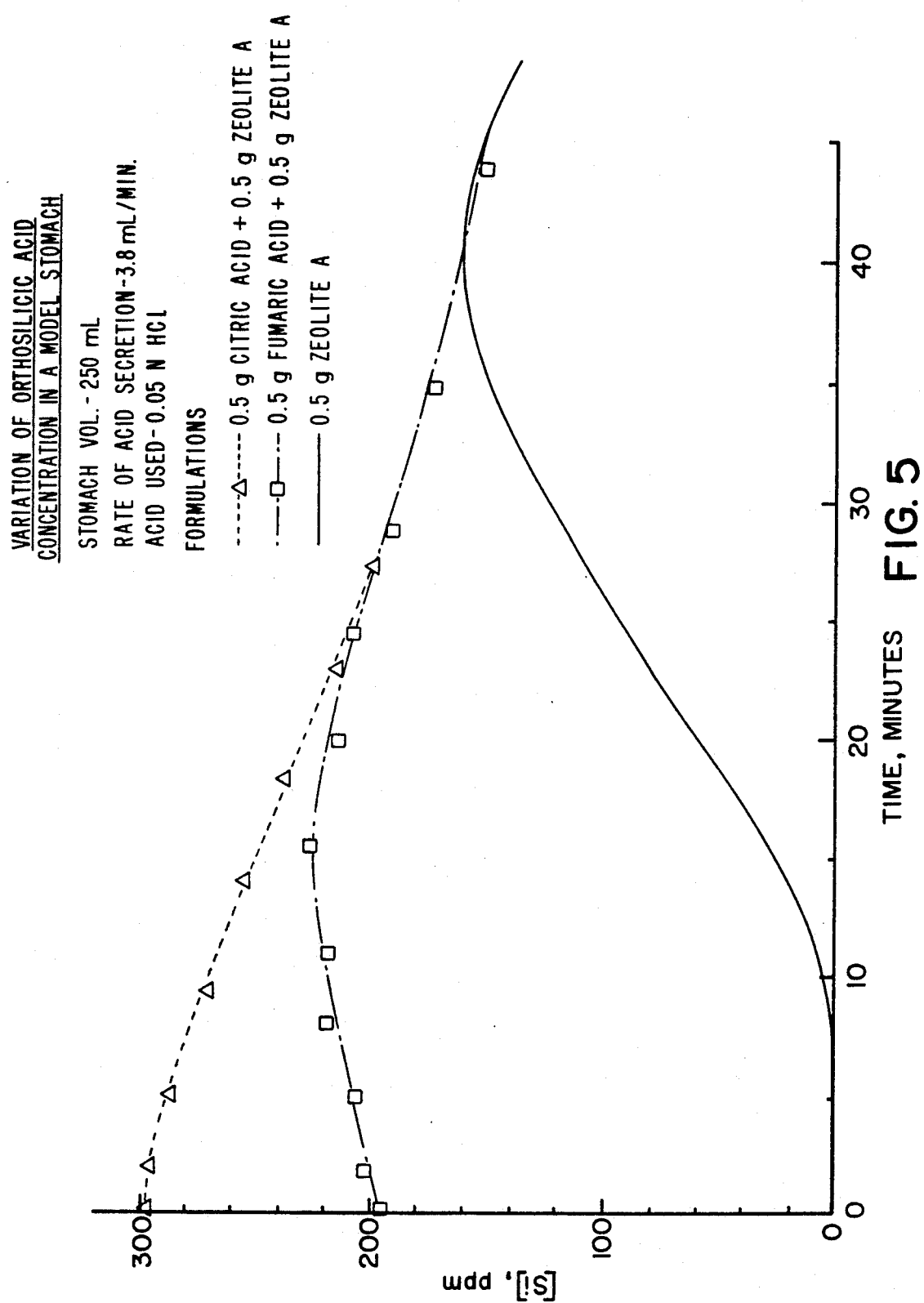

ZEOLITE COMPOSITIONS

This application is a continuation of application Ser. No. 153,456, filed Feb. 8, 1988, now abandoned.

CROSS-REFERENCE TO RELATED APPLICATION

This application is related to application Ser. No. 801,596, filed Nov. 25, 1985 S. M. Laurent and R. M. Sanders for Bone Disorder Treatment now U.S. Pat. No. 4,847,085.

BACKGROUND F THE INVENTION

1. Field of the Invention

This invention relates to the general field of animal therapy. More particularly, this invention is directed to bone disorder therapy in animals, including man. The present invention relates to treatment, prevention, or delay in onset of calcium related bone disorders such as osteoporosis in humans, osteochondrosis in swine and other mammals and poultry, and dyschondroplasia in poultry This invention also pertains to other related bone diseases known in the medical and veterinary sciences, particularly to those related to osteoid calcification disorders.

2. Description of Related Art

Over the years a wide variety of experiments have been conducted throughout the world utilizing zeolites of many different types in the feeding of animals for varying reasons. Most of these experiments have been in the fields of animal nutrition or animal husbandry, e.g. in increasing the production of food animals or their food products Animals fed zeolites were poultry, cattle, sheep and swine Zeolites fed to the animals were mainly naturally occurring zeolites, i.e. or those zeolites found in nature. Although some degree of success in some areas was achieved, most of the results were unfavorable.

An article by C. Y. Chung et al from *Nongsa Sihom Youngu Pogo* 1978, 20 (Livestock) pp. 77–83 discusses the effects of cation exchange capacity and particle size of zeolites on the growth, feed efficiency and feed materials utilizability of broilers or broiling size chickens. Supplementing the feed of the broilers with naturally occurring zeolites, such as clinoptilolite, some increase in body weight gain was determined. Chung et al also reported that earlier results at the Livestock Experiment Station (1974, 1975, 1976—Suweon, Korea) Showed that no significant difference was observed when 1.5, 3, and 4.5 percent zeolite was added to chicken layer diets.

U.S. Pat. No. 3,836,676 issued to Chukei Komakine in 1974 discloses the use of zeolites as an adsorbent for adhesion moisture of ferrous sulfate crystals in an odorless chicken feed comprising such crystals and chicken droppings.

Experiments were conducted in Japan on the use of natural zeolite minerals as dietary supplements for poultry, swine and cattle. Significant increases in body weight per unit of feed consumed and in the general health of the animals was reported; (Minato, Hideo, Koatsugasu 5:536, 1968). Reductions in malodor were also noted.

Using clinoptilolite and mordenite from northern Japan, Onagi, T. (Rept. Yamagata Stock Raising Inst. 7, 1966) found that Leghorn chickens required less food and water and gained as much weight in a two-week trial as birds receiving a control diet. No adverse effects on health or mortality were noted. The foregoing Japanese experiments were reported by F. A. Mumpton and P. H. Fishman in the *Journal of Animal Science*, Vol. 45, No. 5 (1977), pp. 1188–1203.

Canada 939,186, issued to White et al in 1974 (U.S. Pat. No. 4,393,082, issued Jul. 12, 1983) discloses the use of zeolites having exchangeable cations as a feed component in the feeding of urea or biuret non-protein nitrogen (NPN) compounds to ruminants, such as cattle, sheep and goats. Natural and synthetic as well as crystalline and non-crystalline zeolites are disclosed. Zeolites tested using in vitro techniques included natural zeolites, chabazite and clinoptilolite and synthetic zeolites X, Y, F, J, M, Z, and A. Zeolite F was by far the most outstanding and zeolite A was substantially ineffective.

An article by W. L. Willis et al entitled *Evaluation of Zeolites Fed to Male Broiler Chickens* published in *Poultry Science*, 61, 438–442 (March, 1982) discloses the feeding of natural zeolites such as clinoptilolite to male broiler chickens in amounts of 1, 2 and 3 weight percent.

In a study at the University of Georgia, both broilers and layers were fed small amounts (about 2%) of clinoptilolite, a naturally occurring zeolite from Tilden, Texas. The egg shells from the hens receiving zeolite were slightly more flexible as measured by deformation, slightly less strong as measured by Instron breaking strength, and had a slightly lower specific gravity. The differences in egg shell quality were very small. This type of zeolite was ineffective in producing a stronger egg shell. An article written by Larry Vest and John Shutze entitled *The Influence of Feeding Zeolites to Poultry Under Field Conditions* summarizing the studies, was presented at *Zeo-Agriculture* '82.

A study by H. S. Nakaue on feeding White Leghorn layers clinoptilolite, reported in *Poultry Science* 60, 944-949 (1981), disclosed no significant differences in egg shell strength between hens receiving the zeolite and hens not receiving the zeolite.

European Patent Application 0119992, published Sep. 26, 1984, discloses the feeding of the natural zeolite, chabazite, to poultry, namely turkeys In a test utilizing 480 tom turkeys, those turkeys fed 2 weight percent chabazite ore showed improved weight gain and feed efficiency over those turkeys fed similar amounts of sodium exchanged zeolite A and calcium exchanged zeolite A; however, the turkeys fed zeolites showed an increase in mortality rate over those turkeys in which no zeolites were fed. The turkeys fed sodium exchanged zeolite A showed significantly less weight gain and less feed efficiency than those turkeys fed no zeolites at all, and the turkeys fed calcium exchanged zeolite A showed about the same weight gain as the control, but had even less feed efficiency than the turkeys fed the sodium exchanged zeolite A.

Japan 59-203450, published Nov. 17, 1984, describes the use of synthetic metal aluminosilicates, preferably type A, type P, type X or type Y zeolites, as feed additives for livestock, pets, cultured fish, etc. with active ingredients consisting of basicity-adjusted aluminosilicates to an equilibrium pH of "10.5 or less"; preferably between 9.5 and 4.5. The feed additives are said to have a digestion-regulating effect, i.e., a high antacid effect in the pH range of 3 to 5. They also are said to appear to be superior as $Co^{++}$ donors and donors of other minerals. In a single experiment of 100 piglets, using 2 weight percent calcium aluminosilicate, either amorphous or type A zeolite, no significant differences between the two forms were observed. Body weight for piglets fed the calcium zeolites showed an increase but feed utilization rate was down slightly.

U.S. Pat. No. 4,537,771 relates to the use of synthetic zeolites as antacids The report to the *Great Lakes Science Advisory Board* of the *International Joint Commission on the Health Implications of Non-NTA Builders*, October, 1980, Windsor, Ontario, Revised March, 1981, summarizes toxicity studies conducted on zeolite A using various animals. Gloxhuber et al also discuss the toxicology of zeolite A; *Chemical Toxicology*, 21:(2), pp. 209-220 (1983). Nolen et al, found no evidence of teratogenicity of zeolite A in rats; *Food and Cosmetic Toxicology*, 21:(5), 697 (1983). Cook et al, *Environ Sci. Tech.*, 16, (No. 6) 344 (1982) discuss zeolite A hydrolysis and degradation. The uptake of acid was measured at pH values in the range of 3-9.

Benke et al discuss urinary silicon excretion of rats following oral administration of silicon compounds including sodium zeolite A; *Food and Cosmetic Toxicology*, 17, pp. 123-127 (1979).

The reference, *Tentative Evaluation of the Health Aspects of Certain Silicates as Food ingredients* (1977), prepared by the Bureau of Foods of the Food and Drug Administration, summarizes the scientific literature from 1920 to 1973 concerning the health aspects of certain silicates as food ingredients.

E. M. Carlisle, *Nutrition Reviews*, 40, (7), 193-198 (1982) discusses the nutritional essentiality of silicon. She also discusses silicon in bone formation in chapter Four of *Silicon and Siliceous Structures in Biological Systems*, Simpson, T. L., ed. B. E. Springer Verlag, New York (1981), pp. 69-94.

Berlyne et al, *Nephron*, 43, 5 (1986), discusses urinary silicon excretion. Charnot et al studied the endocrine interaction of silicon metabolism, *Societe D'Endocronologie*, 397-402 (1971), *Biochemistry of Silicon and Related Products*, Plenum Press, 269-280 (1978).

Merkley, J. W., *The Effect of Sodium Fluoride and Sodium Silicate on Growth and Bone Strength of Broilers, Poultry Science* 62, 798 (1983) discloses that a decrease in humeri strength was observed when one wing of broilers was immobilized for two weeks in the control and sodium fluoride treated groups. The loss of strength was not significant in the sodium silicate group.

Reagan, Luther M., *Effects Of Adding Zeolites To The Diets Of Broiler Cockerels*, Thesis Submitted to Colorado State University, Recommended for Acceptance Apr. 25, 1984, had among its primary objectives "analysis and identification of functional properties of zeolites as they relate to bone breaking strength". No differences were detected in the zeolite treated rations concerning bone strength or bone ash.

Other studies in connection with the aforementioned patent application of Laurent and Sanders indicate that zeolite A has a positive effect upon structural maintenance and strength of bone within six weeks of administration, and that zeolite A in poultry diets causes a reduced incidence and severity of tibial dyschondroplasia (osteochondrosis) and enhanced absorption of $^{47}$calcium; see also Edwards, *Annual Meeting of the Poultry Science Assoc., North Carolina State University* (1986). Research of Laurent et al has also resulted in the discoveries that zeolite A (i) decreases mortality in the rate of laying hens, U.S. Pat. No. 4,610,883; Roland et al, *J. Poultry Sci.*, 64:1177 (1985), Miles et al, *Nutrition Reports International* (1986); (ii) increases quality of poultry eggshells, U.S. Pat. No. 4,556,564; (iii) and reduces heat stress, Influence of ETHACAL Feed Component On Production Parameters Of White Leghorn Hens During High Ambient Temperature, *(paper presented at the Southern Poultry Science Annual Meeting, Atlanta, Ga., Jan. 27-28 (1987).* It has also been discovered that zeolite A inhibits kidney stones or urinary calculi in lambs, Laurent and Pond, U.S. Pat. No. 4,515,780.

SUMMARY OF THE INVENTION

The present invention relates to improved zeolite compositions and their use for increasing bone strength. The compositions of the present invention include a zeolite, preferably zeolite A, and one or more pharmaceutically acceptable acidifying agents. The acidifying agent or agents utilized in the compositions of this invention are selected from pharmaceutically acceptable materials that provide hydrogen ions (protons) when admixed with water, such that the proton concentration in the water is increased. Such agents are exemplified by acids, acid anhydrides, and salts of acids and weaker bases. The acids may be either inorganic or organic in nature. Preferably, the acidifying agent is a water soluble solid.

When used to combat bone disorders, it appears that the zeolite per se is not absorbed from the gastro-intestinal tract. Thus it is believed that the efficacious action of zeolite in combating bone disorders does not involve the combination of ingestion, absorption and transportation of the zeolite per se, to active sites in the body, e.g. osteoid tissue.

The exact nature of the mechanism of action of the zeolite is not known. By its ion exchange properties, the zeolite may alter the exchange of ions such as calcium, and therefore provide a superior absorption of calcium or other ion utilized in bone tissue formation. Alternatively, the zeolite might break down to supply silicon (and perhaps small amounts of aluminum) in forms which are superior to those ordinarily available in the diet. Moreover, the zeolite may provide silicon in some form utilized in the system(s) that are involved in bone formation. The form of silicon made available by zeolite ingestion may be superior to the form or forms of silicon otherwise provided by the diet.

Work to date has not elucidated whether one or more of these possibilities or some other mechanism is involved. It appears that interaction between the gastric mucosa and one or more silicon- and/or aluminum-containing species in the stomach is important, and that for this interaction, acid present in the stomach is involved. Thus, acid secreted by the stomach may alter calcium source(s) and/or the zeolite to increase calcium absorption. Alternatively, the acid may react with zeolite to produce silicon and/or aluminum compositions that are absorbed and utilized in some manner by the body to modify bone metabolism.

The compositions of this invention improve the breakdown of the zeolite or the active material derived therefrom. The acidifying agents within the compositions of this invention are believed to assist the acid-involved interaction(s) of the zeolite that take place in the stomach while the zeolite is present there. The compositions provided by this invention also conserve the zeolite. When the acidifying agents of this invention are not used, the zeolite has a greater tendency to pass from the stomach into the intestine before the acid-involved interaction(s) in the stomach can take place.

The compositions of this invention also reduce the degree of variation in zeolite breakdown. It is known that secretion of gastric acid can vary between individuals, and that the amount of secreted acid tends to be less in older individuals. Furthermore, for any given individual the amount of secreted acid in gastric contents can vary depending on a number of factors, including the time of day and the physiological and emotional state of the individual. Also, the type and quantity of food ingested can have an effect on gastric pH and the ability of gastric acid and the zeolite to intermix and react.

The compositions provided by this invention contain enough acidifying agent to neutralize a substantial amount of the alkalinity provided by the zeolite when it is admixed with an aqueous medium such as gastric juice.

This invention comprises the compositions of this invention and use of the compositions of this invention. Thus, this invention provides new compositions and methods for treating, preventing, or delaying the onset of bone disease, particularly calcium-related disorders of this type. For example, this invention provides a method for increasing the bone strength of an animal having a bone strength less than desired. This invention also comprises a method for treating a calcium-related bone disorder in an animal having such a disorder. These methods comprise administering to such animals a composition of this invention comprising an acidifying agent and a zeolite such as zeolite A. The compositions used in the methods of this invention may be in unit dosage form.

DESCRIPTION OF THE DRAWINGS

FIG. 1 shows the silicon in solution in a model stomach illustrating this invention. The dark, heavy, continuous line beginning above the 300 ppm point on the Y axis is a theoretical plot. It shows the concentration of soluble silicon that would occur upon addition of 0.50 gram of a zeolite A (with instantaneous hydrolysis) to an initial volume of 250 mL of an aqueous system. The initial liquid is changed by a constant addition of 3.8 mL/minute of additional aqueous system, and removal of resulting mixture as described in the Example below. The dashed line is an actual plot of the soluble silicon concentration which occurs upon adding 0.50 gram of zeolite A to an initial volume of 250 mL of water augmented with the addition of additional 0.1 N HCl at the aforementioned 3.8 mL/minute rate. As shown, there is some delay before soluble silicon is made. After about 10 minutes, there is a sharp increase in soluble silicon concentration. At about 25 minutes the concentration of soluble silicon reaches a maximum corresponding to the theoretical plot. Thereafter, the silicon concentration tracks fairly well the theoretical concentration plot. The plot signified with intermittent dot and dashes is an actual plot using 0.05 N HCl. The two actual plots show that the amount of soluble silicon in the synthetic gastric fluid depends on acid concentration. Higher concentrations of acid afford earlier and greater increases in soluble silicon concentration.

FIG. 2 shows the pH variation in the model stomach using 0.50 gram of a zeolite A in the presence or absence of an auxiliary acid. The dots indicate that without auxiliary acid the pH which occurs upon adding the zeolite A to 250 mL of water is above 10.5. There is a sharp drop in pH over time as shown by the additional circles in the drawing. In contrast, in the presence of 0.5 gram of aspartic acid, the initial pH is about 4.5. With the same amount of citric acid, the initial pH is even lower. The filled triangles show the pH values obtained over time using fumaric acid. The initial pH is even lower than with citric acid; viz about 4.0.

FIG. 3 is similar to FIG. 2 except that the concentration of HCl used for simulating secretion acid is 0.05 normal.

FIG. 4 shows the variation in soluble silicon concentration in the model stomach using 0.1 N HCl as the model secretion fluid and 0.5 gram of zeolite A. The solid line shows the pH silicon concentration that occurs when no auxiliary acid is used. The triangles, squares, and circles indicate the pH values obtained over time when 0.5 gram of zeolite A is admixed with respectively, citric acid, fumaric acid and L-aspartic acid. The plot clearly demonstrates that there is much more soluble silicon available early. Accordingly, the addition of auxiliary acid markedly increases the soluble silicon released by hydrolysis of the zeolite A. Similar increases in the availability of other decomposition products such as colloidal aluminum oxides also occurs. Of the three auxiliary acids shown on the plot, citric acid gives the greater increase in soluble silicon and L-aspartic acid gives the least increase in soluble silicon. Fumaric acid gives an intermediate increase.

FIG. 5 is similar to FIG. 4 except that 0.05 N HCl was used. The triangles and squares show the pH values obtained over time when 0.5 gram of the zeolite A was admixed with 0.5 gram of respectively citric acid and fumaric acid As shown, there is a marked increased in availability of soluble silicon at the lower concentration of hydrochloric acid. Seeing the trend between FIGS. 4 and 5 shows that the use of acid/zeolite A mixtures of this invention markedly improves availability of soluble silicon, especially in systems in which the concentration of hydrochloric acid is reduced.

DESCRIPTION OF PREFERRED EMBODIMENTS

This invention comprises as a preferred embodiment, compositions comprising a zeolite effective in improving or maintaining bone health or strength, i.e. a zeolite effective in preventing, treating, or delaying the onset of bone disorders. The zeolite is admixed with a pharmaceutically acceptable acidifying agent such as an acid or acidic salt. Zeolite A is a preferred zeolite for use in this invention. The amount of pharmaceutically acceptable acidifying agent in a composition of this invention substantially reduces the amount of gastric acid required to decompose the zeolite in the stomach of an animal to which the composition is administered.

This invention also comprises as a preferred embodiment a method of increasing the bone strength of an animal having a bone strength lower than desired, said method comprising treating said animal with a relatively small effective amount of a zeolite mixed with a pharmaceutically acceptable acidifying agent.

The invention also comprises as a preferred embodiment a method of treating a bone disorder, such as a calcium-related bone disorder, in an animal having such a disorder, said method comprising treating said animal with a relatively small effective amount of a zeolite mixed with a pharmaceutically acceptable acidifying agent.

The animal treated in the methods of this invention may be a bovine animal, a canine or feline, an ovine animal such as a sheep or goat, or a primate, including man. As examples of the bone disorder treated, there are osteoporosis and the like in humans, osteochondrosis in swine and other mammals and poultry, and dyschondroplasia in poultry.

The methods of this invention can comprise administering the zeolite-acidifying agent admixed in the daily diet of the animal. Alternatively, the zeolite/acidifying agent may be administered in unit dosage form. Oral administration of unit dosage forms is preferred. Zeolite A is a preferred zeolite for this invention.

Zeolites are crystalline hydrated aluminosilicates of alkali and alkaline earth cations, having infinite, three-dimensional structures.

Zeolites consist basically of a three-dimensional framework of $SiO_4$ and $AlO_4$ tetrahedra. The tetrahedra are crosslinked by the sharing of oxygen atoms so that the ratio of oxygen atoms to the total of the aluminum and silicon atoms is equal to two or $O/(Al+Si)=2$. The electrovalence of each tetrahedra containing aluminum is balanced by the inclusion in the crystal of a cation, for example, a sodium ion. This balance may be expressed pressed by the formula $Al/Na=1$. The spaces between the tetrahedra are occupied by water molecules prior to dehydration.

There are a number of different types of zeolites. Some zeolites are found in nature and are made synthetically. Other zeolites are made only synthetically. Zeolite A is not found in nature and is made only synthetically.

Zeolite A may be distinguished from other zeolites and silicates on the basis of their composition and X-ray powder diffraction patterns and certain physical characteristics. The X-ray patterns for these zeolites are described below. The composition and density are among the characteristics which have been found to be important in identifying these zeolites.

The basic formula for all crystalline sodium zeolites may be represented as follows:

$$Na_2O.Al_2O_3.xSiO_2.yH_2O.$$

In general, a particular crystalline zeolite will have values for "x" and "y" that fall in a definite range. The value "x" for a particular zeolite will vary somewhat since the aluminum atoms and the silicon atoms occupy essentially equivalent positions in the lattice. Minor variations in the relative number of these atoms do not significantly alter the crystal structure or physical properties of the zeolite. For zeolite A, the "x" value normally falls within the range $1.85\pm0.5$.

The value for "y" is not necessarily an invariant for all samples of zeolites. This is true because various exchangeable ions are of different size, and, since there is not major change in the crystal lattice dimensions upon ion exchange, the space available in the pores of the zeolite to accommodate water molecules varies.

The average value for "y" for zeolite A is 5.1. The formula for zeolite A may be written as follows:

$$1.0\pm0.2\ Na_2O.Al_2O_3.1.85\pm0.5\ SiO_2.yH_2O.$$

In the formula, "y" may be any value up to 6.

An ideal zeolite A has the following formula:

$$(NaAlSiO_4)_{12}.27H_2O$$

Among the ways of identifying zeolites and distinguishing them from other zeolites and other crystalline substances, the X-ray powder diffraction pattern has been found to be a useful tool. In obtaining the X-ray powder diffraction patterns, standard techniques are employed. The radiation is the K doublet of copper and a Geiger counter spectrometer with a strip chart pen recorder is used. The peak heights, I, and the positions as a function of $2\theta$ where $\theta$ is the Bragg angle, are read from a spectrometer chart. From these, the relative intensities $100\ I/I_o$, where $I_o$ is the intensity of the strongest line or peak and d the interplanar spacing in angstroms corresponding to the recorded lines are calculated.

X-ray powder diffraction data for a sodium zeolite A are given in Table I.

TABLE I

| X-RAY DIFFRACTION PATTERN FOR ZEOLITE A | | |
|---|---|---|
| $h^2 + k^2 + l^2$ | d (Å) | $\dfrac{100\ I}{I_o}$ |
| 1 | 12.29 | 100 |
| 2 | 8.71 | 70 |
| 3 | 7.11 | 35 |
| 4 | 6.15 | 2 |
| 5 | 5.51 | 25 |
| 6 | 5.03 | 2 |
| 8 | 4.36 | 6 |
| 9 | 4.107 | 35 |
| 10 | 3.895 | 2 |
| 11 | 3.714 | 50 |
| 13 | 3.417 | 16 |
| 14 | 3.293 | 45 |
| 16 | 3.078 | 2 |
| 17 | 2.987 | 55 |
| 18 | 2.904 | 10 |
| 20 | 2.754 | 12 |
| 21 | 2.688 | 4 |
| 22 | 2.626 | 20 |
| 24 | 2.515 | 6 |
| 25 | 2.464 | 4 |
| 26 | 2.414 | >1 |
| 27 | 2.371 | 3 |
| 29 | 2.289 | 1 |
| 30 | 2.249 | 3 |
| 32 | 2.177 | 7 |
| 33 | 2.144 | 10 |
| 34 | 2.113 | 3 |
| 35 | 2.083 | 4 |
| 36 | 2.053 | 9 |
| 41 | 1.924 | 7 |
| 42 | 1.901 | 4 |
| 44 | 2.858 | 2 |
| 45 | 1.837 | 3 |
| 49 | 1.759 | 2 |
| 50 | 1.743 | 13 |
| 53 | 1.692 | 6 |
| 54 | 1.676 | 2 |
| 55 | 1.661 | 2 |
| 57 | 1.632 | 4 |
| 59 | 1.604 | 6 |

The more significant d values for zeolite A are given in Table II:

TABLE II

| MOST SIGNIFICANT d VALUES FOR ZEOLITE A | | |
|---|---|---|
| d Value of Reflection in Å | | |
| 12.1 | ± | 0.2 |
| 8.7 | ± | 0.2 |
| 7.10 | ± | 0.15 |
| 5.50 | ± | 0.10 |
| 4.10 | ± | 0.10 |
| 3.70 | ± | 0.07 |
| 3.40 | ± | 0.06 |
| 3.29 | ± | 0.05 |
| 2.98 | ± | 0.05 |
| 2.62 | ± | 0.05 |

Occasionally, additional lines not belonging to the pattern for the zeolite appear in a pattern along with the X-ray lines characteristic of that zeolite. This is an indication that one or more additional crystalline materials are mixed with the zeolite in the sample being tested. Small changes in line positions may also occur under these conditions. Such changes in no way hinder the identification of the X-ray patterns as belonging to the zeolite.

The particular X-ray technique and/or apparatus employed, the humidity, the temperature, the orientation of the powder crystals and other variables, all of which are well known and understood to those skilled in the art of X-ray crystallography or diffraction can cause some variations in the intensities and positions of the lines. These changes, even in those few instances where they become large, pose no problem to the skilled X-ray crystallographer in establishing identities. Thus, the X-ray data given herein to identify the lattice for a zeolite, are not to exclude those materials which, due to some variable mentioned or otherwise known to those skilled in the art, fail to show all of the lines, or show a few extra ones that are permissible in the cubic system of that zeolite, or show a slight shift in position of the lines, so as to give a slightly larger or smaller lattice parameter.

A simpler test described in "American Mineralogist", Vol. 28, page 545, 1943, permits a quick check of the silicon to aluminum ratio of the zeolite. According to the description of the test, zeolite minerals with a three-dimensional network that contains aluminum and silicon atoms in an atomic ratio of $Al/Si = 2/3 = 0.67$, or greater, produce a gel when treated with hydrochloric acid. Zeolites having smaller aluminum to silicon ratios disintegrate in the presence of hydrochloric acid and precipitate silica. These tests were developed with natural zeolites and may vary slightly when applied to synthetic types.

U.S. Pat. No. 2,882,243 describes a process for making zeolite A comprising preparing a sodium-aluminum-silicate water mixture having an $SiO_2:Al_2O_3$ mole ratio of from 0.5:1 to 1.5:1, and $Na_2O$ mole ratio of from 35:1 to 200:1, maintaining the mixture at a temperature of from 20° C. to 175° C. until zeolite A is formed, and separating the zeolite A from the mother liquor.

In one embodiment of this invention, the acidifying agent is a pharmaceutically acceptable organic acid. Amino acids such as L-aspartic acid and glutamic acid can be used in this invention. Unlike glycine and similar acids in which each carboxyl group has an amino group on an alpha carbon, aspartic and glutamic acid has a carboxyl group which does not have an alpha amino group. This isolated carboxyl is non-zwitterionic, and therefor L-aspartic acid and similar materials with an isolated carboxyl comprise a preferred class of organic acids. The acid may be ascorbic acid, or some other acidic substance in which the acid function is derived from groups or radicals other than the carboxylic acid group. Alternatively, the acid may be a monobasic, dibasic, tribasic or tetrabasic carboxylic acid Acids of this type include acetic acid, trimethylacetic acid, lactic acid, benzoic acid, malonic acid, tartaric acid, gluconic acid, citric acid, and the like. Preferably, the acid has three to six carbons such as propionic, pivalic, malic, malonic, maleic, succinic, butyric, valeric, fumaric and glutaric acids.

Thus, the acids employed in this invention may be selected from acids having one of the following formulas: R—COOH, R'(COOH)$_2$, and R"(COOH)$_3$. In these molecular formulas R, R' and R" are organic radicals, e.g. hydrocarbyl radicals, i.e. radicals which are solely composed of carbon and hydrogen. The radicals represented by R, R' and R" may be cyclic or acyclic, straight or branched chain, saturated or unsaturated. The cyclic radicals may be aromatic or non-aromatic. Preferably, the acids contain up to about 10 carbon atoms.

The exact nature or molecular configuration of the acid selected is not critical so long as the acid is appreciably soluble in gastric fluid in the animal being treated and is pharmaceutically acceptable.

The acids may contain other elements than carbon, hydrogen and oxygen; they may contain a halogen, e.g. chlorine or bromine, or sulphur, phosphorus and the like.

Other examples of acids that may be used include decanoic, undecylenic, salicylic, benzenesulfonic, camphorsulfonic, p-chlorobenzensulfonic, 4-methylbicyclo[2.2.2]oct-2-ene-1-carboxylic, cyclopentanepropionic, 1,2-ethanedisulfonic, ethanesulfonic, o-(4-hydroxybenzyl)benzoic, 2-hydroxyethanesulfonic, methanesulfonic, dodecylsulfonic, stearic, 2-naphthylenesulfonic, 3-phenylpropionic, p-toluenesulfonic, gluconic, pantothenic, palmitic, hippuric, mandelic, and caproic acid, and the like. Inorganic acids such as hydrochloric, hydrobromic, sulfuric, orthophosphoric, boric acid and the like can also be used Liquid acids are formulated in a delivery system which substantially prevents interaction of the acid and zeolite prior to ingestion. The solid acids also are preferably formulated according to the skill within the art, to reduce interaction of the components prior to ingestion.

This invention also comprises use of anhydrides which yield acids upon hydrolysis. Thus, acetic anhydride, pyrophosphates, and other similar simple and mixed anhydrides may be used in this invention. Useful anhydrides may be derived from the acids mentioned above.

Acidic salts are another type of acidifying agent utilizable in this invention. Such salts are typically salts of the above acids in which the cation is a weak base. Typical cations of this type are calcium, magnesium, ammonium, and the like. The exact nature of the cation is not critical so long as it does not cause an untoward effect when the salt is administered to the organism being treated according to this invention. The cation should be a weak enough base so that a pH achieved by adding the salt to an aqueous system can lower the pH to a value appreciably below 7. More particularly, salts which give a pH of 5 or lower when one gram molecular weight of the salt is added to a liter of distilled water are preferred. Salts which can be utilized as acidifying agents of this invention are exemplified by sodium hydrogen sulfate, potassium dihydrogen phosphate, calcium dihydrogen phosphate, calcium hydrogen phosphate, tricalcium phosphate, calcium sulfate, calcium hydrogen sulfate, the magnesium analogs of these salts, and the like, e.g. other acid phosphates and sulfates of the type named above.

As indicated above, the compositions of this invention are mixtures comprising a zeolite useful in increasing bone strength, or treating, preventing or delaying the onset of bone disorders. Besides the zeolite or zeolites within the mixtures, there is also incorporated at least one acidifying agent of the type described and illustrated above. The acidifying agent is intentionally added to the zeolite to form the composition.

The hydrochloric acid secreted by the gastric mucosa of the animal being treated does not comprise the acidic component of the compositions of this invention. Thus, for example compositions of this invention which include hydrochloric acid include that acid admixed with the efficacious zeolite prior to administration, to the patient or animal being treated.

The compositions of the invention are dissimilar from acid-washed zeolites per se. As stated above, the mixtures of this invention comprise an acidifying agent and a zeolite. An acid washed zeolite can be utilized in this invention. The acid washed zeolite may replace some or all of the zeolite in the composition described above. For example, a composition of this invention can comprise an acid washed zeolite admixed with citric or aspartic acid.

The compositions of this invention comprise an appreciable amount of acidifying agent. For example, the compositions may contain from about 5 to about 75 weight percent acidifying agent and from about 95 to about 25 percent of zeolite. Compositions somewhat outside this range are also included within this invention. Preferably, compositions of this invention comprise from about 35 to about 65 weight percent acidifying agent and from about 65 to about 35 weight percent zeolite.

These zeolite/acidifying agent mixtures can be used per se or they can be admixed with other substances. As well known in the art, zeolites such as zeolite A can decompose in the presence of aqueous acid. Accordingly, other ingredients may be admixed with the zeolite/acidifying agent mixtures in order to improve the shelf life of unit dosage forms containing the mixtures of this invention. Furthermore, the zeolite/acidifying agent mixtures may also contain adjuvants which facilitate administration of the compositions to the patient or organism being treated.

EXAMPLE

To illustrate this invention data were obtained by monitoring pH and concentration of soluble silicon in a model stomach system. The model stomach system consisted of a Harvard peristaltic pump, a three neck round bottom flask of 250 mL capacity as the stomach, and a fraction collector which collected liquid samples secreted from the stomach cell periodically.

The round bottom flask was placed on a magnetic stirrer. Two of the necks were used for inlet and outlet means respectively. The third one was used as a port for a pH electrode. The pH variation during a test was recorded on a strip chart recorder. During a test, the peristaltic pump delivered a constant flow of acid into the model stomach which was under constant agitation. At the beginning of a test, the model stomach was filled with 250 mL of distilled water and the sample of interest. Typically 10-20 seconds after the starting acid introduction, stomach mixture was secreted into the fraction collector, which was operating in such a mode that it collected the secretion fluid for each 90-second interval.

Samples collected by the fraction collector were diluted immediately with distilled water. The dilution was needed to prevent possible polymerization of silicates. The soluble silicon concentration in the diluted samples was analyzed by a molybdate colorimetric method. The samples were also analyzed for elemental content by induced couple plasma (ICP).

Zeolite A was used in the tests. Anhydrous citric, L-aspartic, and fumaric acids were used as the auxiliary acids. A 3.8 mL/min rate of acid secretion was employed in the investigation. HCl solutions of 0.1 N and 0.05 N concentrations were used as the secretion acid. The dose level of both zeolite A and the auxiliary acid was 0.5 g. Plots of soluble silicon versus time, generated from the model stomach with 0.1 N and 0.05 N HCl as the secretion acid are shown as dotted and broken curves, respectively, in FIG. 1. At 0.50 g zeolite A dose level, the theoretical silicon content in the model stomach described is 0.316 mg/mL. Considering the constant acid secretion rate of 3.8 mL/min, and with the stomach cell behaving like a back mix reactor, the concentration of total silicon should decrease following the solid decay curves shown in the figure. If all the silicon in zeolite A were converted into orthosilicic acid and no polymerization occurred in the model stomach, then the solid curve represents the maximum attainable orthosilicic acid level in stomach juice. The data show that during the first 40 minutes about 45% of the zeolite A, either hydrolyzed or unhydrolyzed, was broken down. At the acidity level of 0.1 N HCl, 60% of the secreted zeolite A was hydrolyzed and all the silicon in zeolite A was converted into soluble silicon stoichiometrically. At the acidity of 0.05 N HCl, the conversion dropped to 26%.

Acidity of stomach secretion fluid equivalent to 0.1 N HCl is infrequent and acidity of 0.05 N HCl equivalence is found only in very young persons. For a substantial percentage of the population, especially with older people, the acidity of stomach secretion fluid is much lower. The data suggest that even at the most optimal conditions, not all the silicon in zeolite A can be converted into the form of orthosilicic acid. Under normal conditions the potential efficacy of zeolite A as a source of orthosilicic acid is not fully utilized.

FIGS. 2 and 3 show the change in stomach pH in the model stomach with the acidity of secretion acid of 0.1 N HCl and 0.05 N HCl, respectively. The data show that in the absence of an auxiliary acid, due to the presence of zeolite A, stomach pH may increase to around 11. However, when the dose was formulated with 0.5 g of zeolite A and 0.5 g of auxiliary citric, fumaric, or L-aspartic acid, the stomach pH was in the 4-5 range.

FIGS. 4 and 5 show the changes in soluble silicon concentration found in fluid secreted from the model stomach. Again, data shown in FIG. 4 were generated with 0.1 N HCl and data given in FIG. 5 were obtained from experiments when 0.05 N HCl was used as secretion acid. The silicon concentration, [Si], versus time plots generated from using zeolite A alone were also included for reference purposes.

It is clear that the soluble silicon releasing pattern of zeolite A can be altered by the incorporation of an auxiliary acid. It appears that citric acid is more effective than fumaric acid which in turn is more effective than L-aspartic acid. The data show that by incorporating 0.5 g of citric acid into a dosage of 0.5 g zeolite A, soluble silicon was generated almost instantaneously. Also, the concentration of soluble silicon detected closely resembled the theoretical values.

Similar results are obtained when the compositions utilized above are substituted by similar compositions containing from 5 to 75 weight percent citric, fumaric and aspartic acids and from 25 to 95 weight percent zeolite A.

Similar results are also obtained when from about 5 to 75 weight percent of the composition of this invention is propionic, malic, malonic, maleic, succinic, glutaric, or ascorbic acid and the remainder is zeolite A. Similar results are obtained when the compositions utilized contain 5 to 75 weight percent calcium dihydrogen phosphate, calcium hydrogen phosphate or tricalcium phosphate or the analogous magnesium salts and the remainder is zeolite A. The compositions may be in unit dosage form. The preferred unit dosage forms are substantially free of adjuvant or excipient materials that will neutralize acid in gastric juice while the zeolite is in the gastric juice. Still more preferably, the unit dosage forms have a number of milliequivalents of $H^+$ equal to or in excess the milliequivalents of basic ions obtained when the dosage form is added to the gastric juice such, that the acidifying agent supplying the $H^+$ prevents the unit dosage form from causing an increase in the pH of gastric juice while the zeolite is present in the gastric juice.

In view of the above detailed description, a skilled practitioner can make modifications or substitutions of the subject matter disclosed above without departing from the scope and/or spirit of the appended claims.

We claim:

1. An acid-modified zeolite A composition suitable for use as an agent in pharmaceutical preparation for the treatment, prevention or delay in onset of a bone disorder in an animal; said composition comprising a mixture of zeolite A and a pharmaceutically acceptable acidifying agent, the amount of said agent in said composition being sufficient to maintain a pH in the stomach of an animal ingesting said composition at less than 5 and substantially reduce the amount of gastric acid required to decompose said zeolite while said zeolite is present in the stomach of the animal to which said acid-modified composition has been administered, said composition being in unit dosage form and substantially free of adjuvant or excipient materials that will neutralize acid in gastric juice while said zeolite is in said gastric juice.

2. The composition of claim 1 wherein said acidifying agent is a pharmaceutically acceptable organic acid.

3. The composition of claim 2 wherein said acid is ascorbic acid.

4. The composition of claim 3 wherein said acid is a carboxylic acid solely composed of carbon, hydrogen, and oxygen.

5. The composition of claim 4 wherein said acid is polybasic.

6. The composition of claim 5 wherein said acid is citric acid.

7. The composition of claim 5 wherein said acid is a dibasic acid.

8. The composition of claim 7 wherein said acid has three to five carbon atoms.

9. The composition of claim 8 wherein said acid is selected from the class consisting of propionic, malic, malonic, maleic, succinic, fumaric, and glutaric acid.

10. The composition of claim 1 wherein said acidifying agent is selected from the class consisting of pharmaceutically acceptable inorganic acids, and pharmaceutically acceptable acidic salts of an inorganic acid and a weaker base.

11. An acid-modified zeolite A composition suitable for use as an agent in pharmaceutical preparations for the treatment, prevention or delay in onset of a bone disorder in an animal; said composition comprising a mixture of zeolite A and a pharmaceutically acceptable acidifying agent, the amount of said agent in said composition being sufficient to maintain a pH in the stomach of an animal ingesting said composition at less than 5 and substantially reduce the amount of gastric acid required to decompose said zeolite while said zeolite is present in the stomach of an animal to which said acid-modified composition has been administered, said composition being in unit dosage form and substantially free of adjuvant or excipient materials that will neutralize acid in gastric juice while said zeolite is in said gastric juice said unit dosage being sufficient to provide a number of milliequivalents of $H^+$ at least equal to the milliequivalents of basic ions obtained when said unit dosage form is added to gastric juice, said acidifying agent being present in an amount sufficient to prevent said unit dosage form from causing an increase in the pH of said gastric juice while said zeolite is present in said gastric juice.

12. The composition of claim 11 wherein said acidifying agent is a pharmaceutically acceptable organic acid.

13. The composition of claim 12 wherein said acid is ascorbic acid.

14. The composition of claim 13 wherein said acid is a carboxylic acid solely composed of carbon, hydrogen, and oxygen.

15. The composition of claim 14 wherein said acid is polybasic.

16. The composition of claim 15 wherein said acid is citric acid.

17. The composition of claim 15 wherein said acid is a dibasic acid.

18. The composition of claim 17 wherein said acid has three to five carbon atoms.

19. The composition of claim 18 wherein said acid is selected form the class consisting of propionic, malic, malonic, maleic, succinic, fumaric, and glutaric acid.

20. The composition of claim 11 wherein said acidifying agent is selected from the class consisting of pharmaceutically acceptable inorganic acids, and pharmaceutically acceptable acidic salts of an inorganic acid and a weaker base.

* * * * *